United States Patent [19]

Parra

[11] Patent Number: 5,137,029
[45] Date of Patent: Aug. 11, 1992

[54] NON-INVASIVE OPHTHALMIC DIAGNOSTIC METHOD AND APPARATUS

[76] Inventor: Jorge M. Parra, 7332 Grand Blvd., New Port Richey, Fla. 34652

[21] Appl. No.: 588,985

[22] Filed: Sep. 26, 1990

Related U.S. Application Data

[63] Continuation-in-part of Ser. No. 569,121, Aug. 17, 1990.

[51] Int. Cl.$^5$ ............................................. A61B 7/00
[52] U.S. Cl. ................................... 128/745; 128/773
[58] Field of Search ............... 351/200, 219, 201, 202, 351/211; 128/645, 646, 647, 649, 687, 688, 689, 691, 694, 630, 773, 668, 79, 745

[56] References Cited

U.S. PATENT DOCUMENTS

| | | | |
|---|---|---|---|
| 4,316,271 | 2/1982 | Evert | 73/644 |
| 4,572,199 | 2/1986 | LaCourse | 128/688 |
| 4,796,632 | 1/1989 | Boyd | 128/662.03 |
| 4,796,639 | 1/1989 | Snow | 128/719 |
| 4,838,681 | 6/1989 | Paulidis | 351/211 |
| 4,907,595 | 3/1990 | Strauss | 128/691 |
| 4,928,705 | 5/1990 | Sckhar | 128/773 |
| 4,951,671 | 8/1990 | Coan | 128/645 |

FOREIGN PATENT DOCUMENTS 0164730 12/1985 European Pat. Off. ............ 128/645

OTHER PUBLICATIONS

Ultrasonic Investigations in Ophthamology, E. J. Giglo, pp. 87–96, *Ultrasonic in Clinical Diagnosis*, ed. P. N. J. Wells.

*Primary Examiner*—Francis Jaworski
*Assistant Examiner*—Robert L. Nasser, Jr.
*Attorney, Agent, or Firm*—Jim Zegeer

[57] ABSTRACT

Sound made by the flow of blood in the retinal blood vessel system of the human eye which, when the exposed portion thereof is partially or completely immersed in a body of acoustically transmissive liquid (ATL), are directly coupled to the acoustically transmitted liquid and thus launched into the acoustically transmitted liquid. The blood vessel system of the human eye has a unique acoustic signature in the infrasonic range. Injured or diseased eyes have unique acoustic signatures e.g., sound they make, which are launched into the ATL and thus each individual retinal blood flow system make or produce a unique pattern of noise or sounds which are normally inaudible, but when immersed in a body of water can be detected by hydrophones or underwater microphones. The invention has use in medical diagnosis of eye ailments as well as providing a baseline for future diagnosis of human eyes.

15 Claims, 4 Drawing Sheets

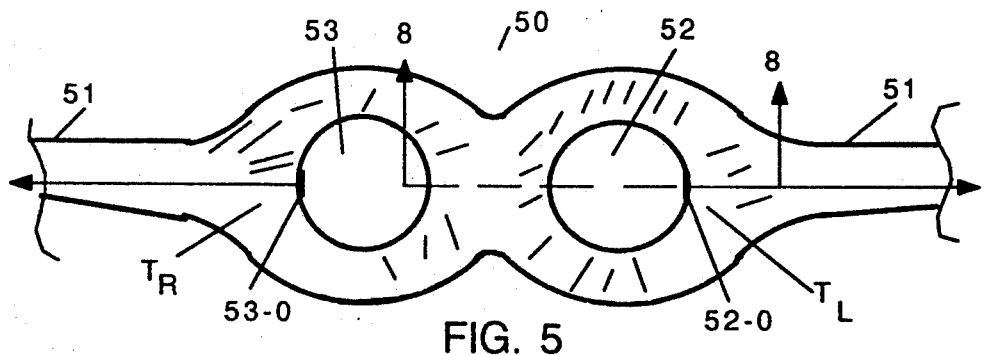
FIG. 5
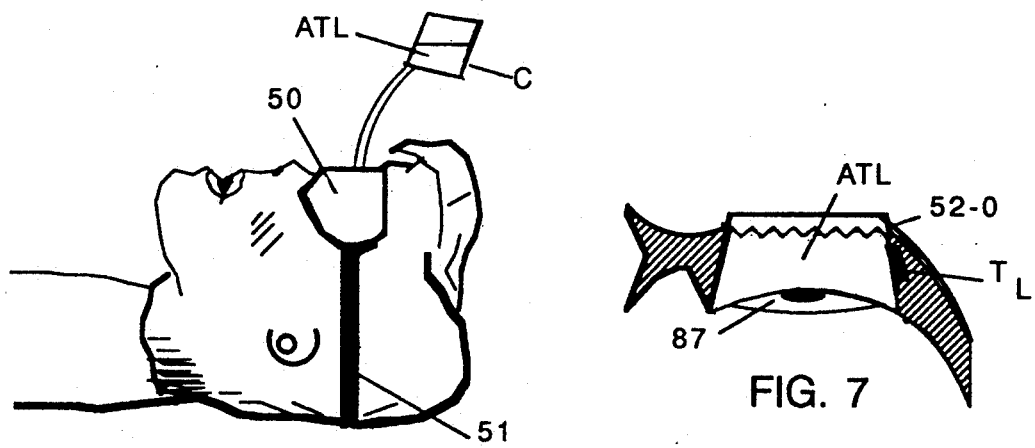
FIG. 6
FIG. 7
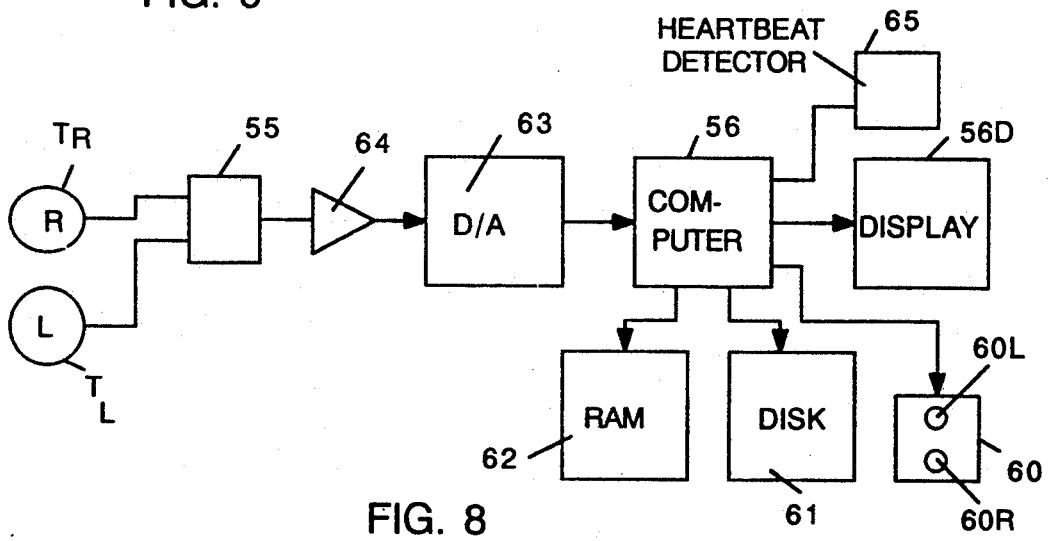
FIG. 8

NON-INVASIVE OPHTHALMIC DIAGNOSTIC METHOD AND APPARATUS

REFERENCE TO RELATED APPLICATIONS

This invention is a continuation-in-part of my application Ser. No. 07/569,121 filed Aug. 17, 1990 for "NON-INVASIVE DIAGNOSTIC METHOD AND APPARATUS" now U.S. Pat. No. 5,031637.

BACKGROUND AND BRIEF DESCRIPTION OF THE INVENTION

Stethoscopes and like apparatus have been used for many years to listen to sounds made by the human body and to make diagnostic analysis of various conditions in the human body. The sounds produced are typically in the sonic range and while stethoscopes are, obviously, widely used by the medical profession, the types of analysis and uses for such apparatus is relatively limited primarily to the chest cavity area (e.g., breathing and gas flow in the lungs, etc.) and for blood pressure readings in the cardiovascular system.

My above-identified U.S. Pat. No. 5,031,637 is directed to a non-invasive diagnostic apparatus and method wherein the human body or a portion thereof is placed in a body of an acoustically transmissive liquid, such body of acoustically transmitting liquid being contained in a container preferably having sidewalls formed of or coated with acoustically absorbent material. One or more hydrophones are located in the body of liquid to detect or "listen" to sounds, such as cardiovascular sounds, gas flow and skeletal sounds made by body movements. These sounds are passed through a preamplifier, a bandpass filter and discriminator, the function of which may be performed by microprocessors to a recorder and/or display device. The recorder can record body sounds much in the fashion of an strip chart recorder used for EKG and/or EEG. Typical pool water with chlorine, or salt water, or oils, such as vegetable oils can be used for the acoustically transmissive medium. In addition to audible sounds, the method and apparatus are particularly useful for listening to infrasonic or subsonic sounds. According to my above application, the subject is placed or immersed in the body of acoustically transmissive liquid in a container having acoustically absorbing walls so that there are no unwanted reflections of sounds launched in the water from the human body reflecting off of the walls. One or more hydrophones located in the body of water are used to detect the sonic energy launched by the human body. The human in the body of acoustic liquid is instructed to go through a particular sequence of movement, for example, the arms, (flexion, extension, abduction, adduction), or the back, or legs (inversion eversion), etc. and record is made the sounds emitted during each of the movements of the specific body parts or the specific movement made by a given patient. For example, an athlete may be asked to bend his or her knee (flexion, extension), elbow (flexion, extension) and the like and a record is made of the sounds generated and launched into the acoustically transmissive liquid. Similar recordings are made for a large number of individuals to provide a norm of the movements of a particular body part in a particular direction and/or at a particular rate of speed. These records then form a database which may be stored in the computer database and used to detect departures from the normal sounds made and thereby provide the physician with a greater body of knowledge to enable successful treatment for the patient.

THE PRESENT INVENTION

Sound made by the flow of blood in the retinal blood vessel system of the human eye which, when the exposed portion thereof is partially or completely immersed in a body of acoustically transmissive liquid (ATL), are directly coupled to the acoustically transmitted liquid and thus launched into the acoustically transmitted liquid. One or more transducers are mounted in the ATL and coupled to electronic processing systems for diagnosis and display. Piezo plastics ($PVF_2$, for example) having a flat frequency response in the infrasonic range are preferred. The blood vessel system of the human eye has a unique acoustic signature in the infrasonic range. Injured or diseased eyes or eyes reflecting macular degeneration have unique acoustic signatures e.g., sounds they make, which are launched into the ATL and thus each individual retinal blood flow system make or produce a unique pattern of noise or sounds which are normally inaudible, but when immersed in a body of water or neutral eye wash liquid, can be detected by hydrophones or underwater microphones. The invention has use in medical diagnosis of eye ailments as well as providing a baseline for future diagnosis of human eyes.

The above and other objects, advantages and features of the invention will become more apparent when considered with the following specification and accompanying drawings wherein:

FIG. 1 is a perspective isometric view of the apparatus disclosed in my above-identified application, FIG. 2 is a diagrammatic illustration of a few movements of the body at the joints (from Wedding et al. "Medical Terminology", copyright 1988), FIG. 3 is a block diagram, FIG. 4 is a detailed block diagram, FIG. 5 is a partial top view of the ATL reservoir according to the invention, FIG. 6 is a side elevational view of a patient with the ATL reservoirs, FIG. 7 is a partial sectional view taken on lines 7—7 of FIG. 6, FIG. 8 is a block diagram of a circuit incorporating the invention, FIG. 9 is a sectional view of a further embodiment of the ATL reservoir and transducer, FIG. 10 illustrates a commercial eye cup eyewash container equipped with a transducer on the head of a patient or subject, FIG. 11 is a sectional view of the eye cup eyewash container shown in FIG. 10, and FIG. 12 illustrates the eye cup and transducer assembly on an eye.

DETAILED DESCRIPTION OF THE INVENTION

Figure 1:
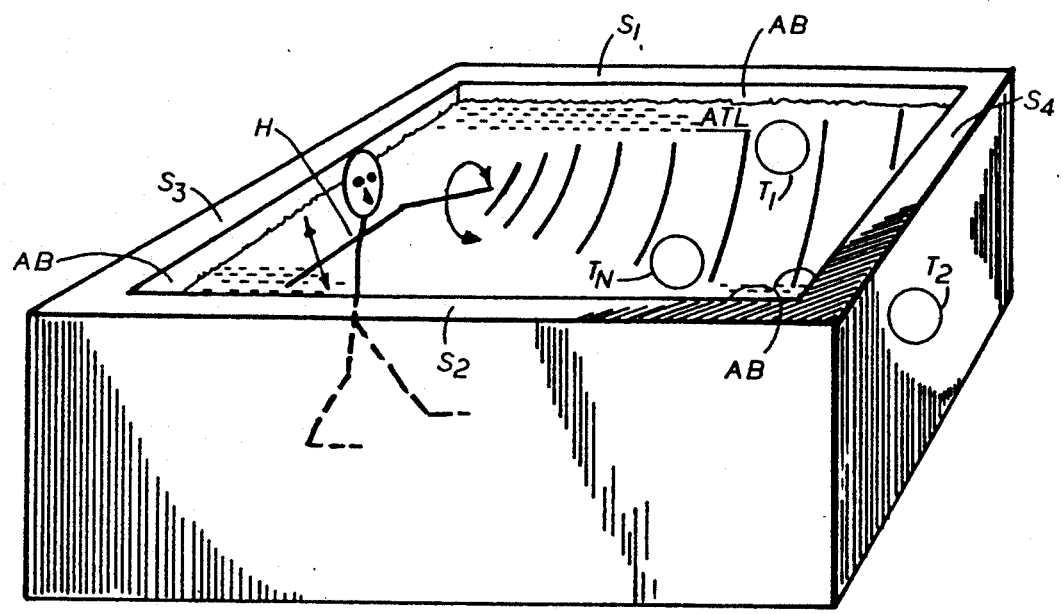

Referring to FIG. 1, a vessel or container 10 which is of sufficient size to at least hold a portion of a human body therein such that the portion can be voluntarily articulated by the human without engaging or contacting the sidewalls. In the illustrated embodiment, the vessel 10 is a large tank in which a human H is immersed up to the neck line. In a preferred embodiment, the sidewalls S1, S2, S3 and S4 and bottom are preferably formed of or coated with an acoustic absorber AB so that there are substantially no reflections of acoustic energy from the sidewalls and that any acoustic energy launched by the human H body, or body parts, are received directly by one or more hydrophones T1, T2...TN, which are oriented to face the human's body. (While the specimen or patient is a human, it will be appreciated that the same techniques may be used in connection with race horses, dogs, cats and other animals, but, in this preferred embodiment, the invention is particularly applicable to diagnostic purposes for use with humans).

Figure 2:
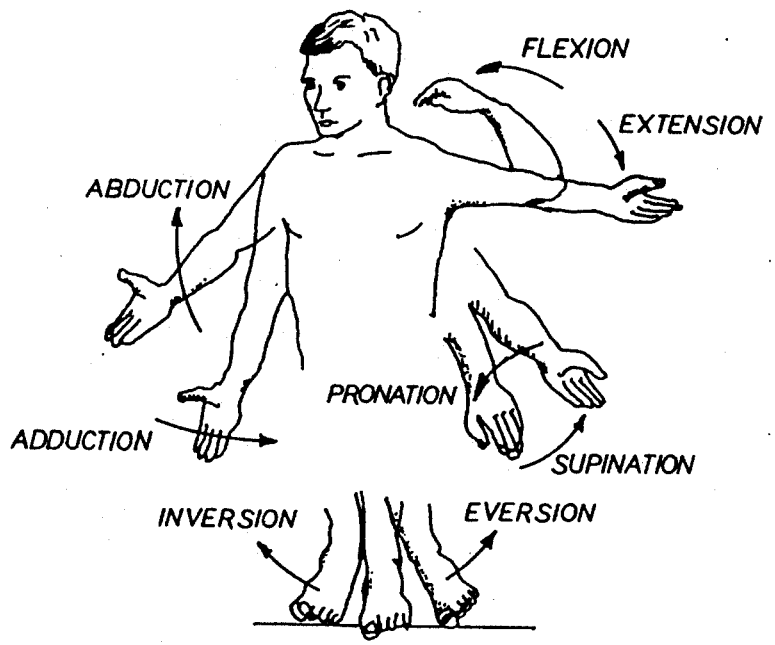

Various movements made by the body at the joints are illustrated in FIG. 2 and these generate sounds. According to the invention, sounds emitted from the human body caused by movements of the skeletal portion (skeletal sounds) and/or blood flow (cardiovascular sounds) and/or air flow are detectable using the invention.

Noises made by the flow of blood in the human cardiovascular system and skeletal noises in the joints of a human skeleton provide a wide variety of sounds (mostly infrasonic) which, when the human body is partially or completely immersed in a body of an acoustically transmissive liquid medium ATL such as water, vegetable oil, etc., are directly coupled to the liquid medium and thus launched into the liquid medium. Each joint, for example, has a unique acoustic signature. Joints which are injured or diseased can have their own unique acoustic signatures or sounds they make which are launched into the liquid medium. Thus, each individual skeletal system makes or produces a unique pattern of sonic energy or noise which are normally infrasonic or but, when immersed in a body of acoustically transmissive liquid such as water, vegetable oil and the like, can be detected by hydrophones or underwater microphones T1, T2...TN.

In FIG. 1, the hydrophone or transducers T1, T2...TN may comprise of one or a plurality of different microphones, and are each referred to herein as acoustic transducers and they convert acoustic energy transmitted in the body of acoustically transmissive liquid ATL.

Figure 3:
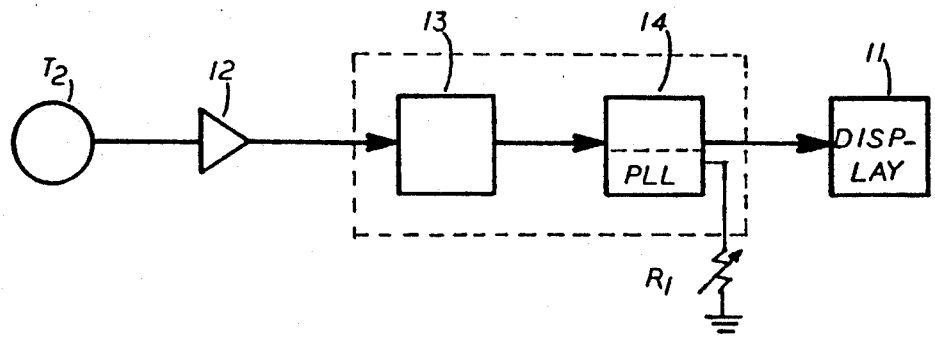

Acoustic transducers T may be positioned in the body of acoustically transmissive liquid ATL or a wall of vessel 10 and converts all sonic energy to electrical signals. As shown in the block diagram of FIG. 3, the electrical signals produced by transducer T2 are amplified by preamplifier 12 and supplied to a bandpass filter 13, the output of which is supplied to a discriminator 14 and then to a display or recorder 11. The bandpass filter removes unwanted background noise and interference and passes the desired cardiovascular and/or skeletal sounds. The configuration of the filter is in a cascaded high-pass/low-pass configuration to maximize attenuation outside the desired frequency. While there are some sounds that are in the audible range, typical sounds made by the movement of the human skeletal system are in the subsonic or infrasonic range and thus in the preferred embodiment, the bandpass filter is designed to restrict frequencies to this. Moreover, the solid state discriminators include a phase lock loop PLL which is adjustable or programmed by adjustable resistor R1 to pass a predetermined discrete pattern of electrical signals constituting a sonic profile, signature or imprint of the movement of a selected body part. For example, the up and down sidewise movement (abduction-adduction) of the human arms shown in FIG. 1 is movement of the humerus bone or upper arm bone in the shoulder, movement of the fibial relative to the femur e.g., the knee joint, provides subsonic sounds (apart from the audible snapping of joints) which are unique and distinctive.

Figure 4:
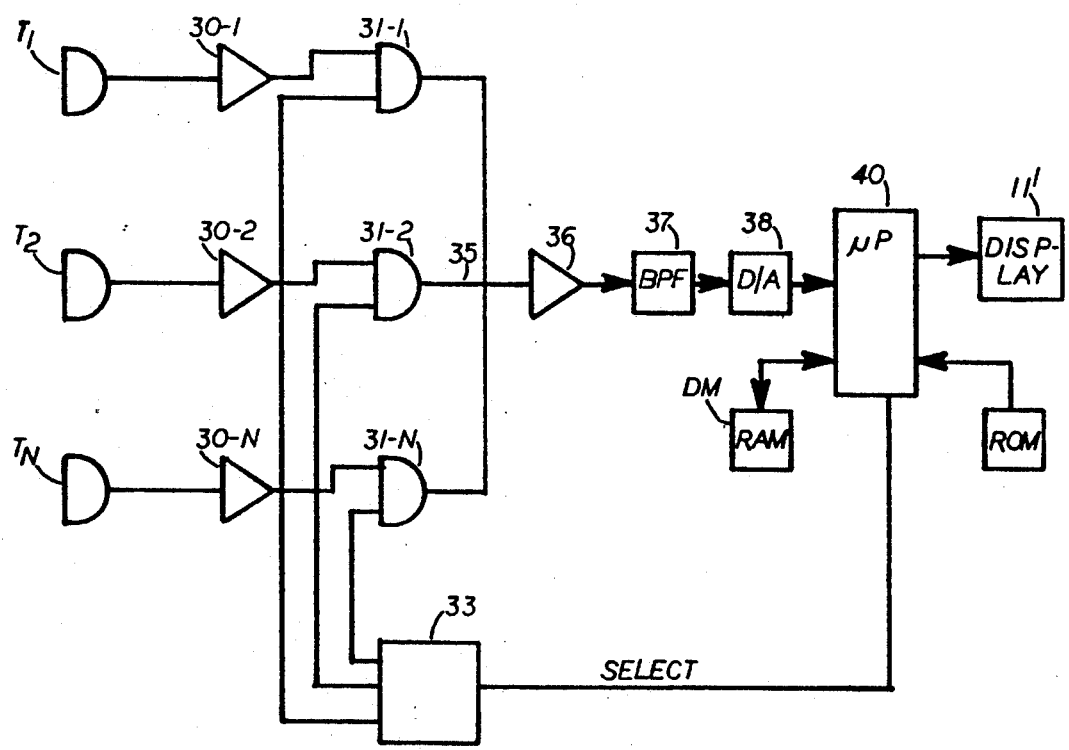

Referring now to in FIG. 4, a plurality of transducers T1, T2...TN have their outputs amplified in preamplifiers 30-1, 30-2...30-N. While the multiplexing operation can be performed either at the transducer head or in an electronic's compartment, in this embodiment, the multiplexing operation is performed at the transducer head. In this case, the gates 31-1, 31-2...31-N receive gate signals from counter 33 via line "select". The gated analog signals are coupled by a coaxial cable 25 to an amplifier 36, bandpass filter 37BPF and analog-to-digital converter 38. The digital signals constituting the multiplexed output for the individual transducers are then supplied to the microprocessor 40 which controls the "select" line and, in turn, the counter 33.

In this case, the microprocessor 40 performs the filter and discriminator functions discussed earlier, to identify and classify the acoustic signatures from the different body systems, and also operates the display 71 which may be a CRT, LCD, plasma, or EL display.

In addition, a read-only memory ROM is provided for storing sonic profiles of large number of joints or cardiovascular flow in particular parts of the body which is used to compare with the incoming acoustic or sonic profiles so as to identify the sounds and the cardiovascular or skeletal system from which they emanate. At the same time, microprocessor 40 stores for short term use data in a random access memory DM.

The entire spectrum of sonic signals for each joint in the skeletal system or the cardiovascular system and each part of the body may be detected, digitized and stored in a computer memory. For this purpose, a digital-to-analog converter DA is provided for converting each acoustic signature to a digital signal and processed by microprocessor MP and stored in a digital memory DM. Moreover, each acoustic signature may be analyzed and compared with a standard acoustic signature which has been derived from analysis of a large number of acoustic signatures. For example, a large number of individuals may be placed in vessel 10, and asked to move a particular part of their body in a particular fashion. For example, the human H shown in FIG. 1 is asked to point his right arm directly outwardly from the side and then move it in an arc up and down (while the shoulder joint is, of course, below the surface of the acoustically transmissive liquid ATL). See FIG. 2 for a sample of the various movements. A large number of individuals are asked to do the same articulation of their right arm. The acoustically recorded signatures for each individual are then analyzed to establish a norm or "standard" which may be stored in a read only memory ROM, along with other fixed program files. The standard may be according to age, sex, physical size (e.g., skeletal size). As another example, a group of individuals may each be asked individually to insert their leg into the acoustic transmissive liquid AT and hold it stationary and the transducer 11 used to detect the infra subsonic signals made by the coursing of the blood flow through the cardiovascular system and thereby derive an acoustic signature to establish as a standard comparison. In like manner, individuals having a particular ailment may be asked to immerse a part of their body into the acoustically transmissive liquid and those known ailments then utilized as a base for stablishing a characteristic departure from the standard. Numerous other examples of similar character may be given but it is believed that the above is sufficient to establish the broad implication and applications of the invention.

Since the acoustic signatures for different skeletal areas and parts of the human and flows in different parts of the cardiovascular system have their own characteristic acoustic signatures, transducers may constituted by a plurality of hydrophones T1, T2...TN for example, and bandpass filters, one utilized for example, for selected cardiovascular signals and one used for selected skeletal signals. Large numbers of individual channels may be utilized, each attuned to a particular skeletal sound or a particular cardiovascular sound. Finally, different combinations of skeletal and cardiovascular sounds may be utilized to detect and identify a particular individual or to detect and identify particular ailments and/or symptoms of ailments.

THE PRESENT INVENTION

The present invention is directed to ophthalmic applications of the principles disclosed above and in my above-identified application. Referring to FIG. 5, a separate acoustically transmissive liquid reservoir is provided for each eye by swimmer-like goggles 50 which is formed of soft flexible elastomeric material so as to closely conform to and be shaped by skin, tissue and bone structures surrounding each eye cavity. Because it is made of a soft form-retaining material, it serves as an acoustic absorber and acoustic reflections are eliminated or minimized. An elastic headband 51 draws each conforming structure 52, 53 into a snug and sealing engagement with each eye cavity so that the reservoirs 52 and 53 can be filled with acoustically transmissive liquid from container C. Although the reservoirs are shown as circular, they could just as well be square.

The inner wall surfaces of the reservoirs are treated with acoustically absorbent material, but the small size of the reservoirs and soft rubber assures the low frequency of interest assure that there are little or no reflections. Transducers $T_R$ and $T_L$ and are mounted in the outside sidewalls 52-0 and 53-0, and are preferably hydrophones made of piezoelectric plastic (such $PVF_2$ sold by the Pennwalt Corporation under their KynarR brand pizeo plastic or as the polarized homopolymer of vinylidene fluoride (PVDF)) materials which are well known in the art. One commercial source of these materials is Pennwalt Corporation of Pennsylvania. The transducers are connected to the circuit shown in FIG. 8 which has been tuned for ophthalmic frequencies and acoustic patterns. These materials are preferred because of their good (flat) response in the low infrasonic range for retinal blood flow analysis.

Referring to FIG. 8, alternatively, the transducers $T_R$ and $T_L$ convert sonic energy in the ATL in each reservoir 52, 53 are electrically connected to a computer controlled selector switch 55. Although parallel channels (of FIG. 3 type) could be used for signal processing, the arrangement shown in FIG. 8 is preferred. Computer 56 controls the operation of selector switch 55 so that alternate ones of transducers $T_R$ and $T_L$ are connected to the processing system. A selector switch 60 may be provided so that an operator can select 60R or 60L to select the left or right eye for examination and analysis.

To establish a library of ophthalmic acoustical signatures, a large number of eyes are acoustically examined and their infrasonic signatures recorded with the apparatus of FIG. 8. Acoustic signatures of a large number of healthy eyes are analyzed to form a composite or standard acoustic signature for healthy eyes and stored in memory RAM or ROM. Likewise, the acoustic signature of a large number of eyes having various eye ailments ranging from various retinal disorders such as retinal detachment, bleeding, loss of or reduced blood flow, etc., incipient problems related to small hemorrhaging that do not go into the eye fluid and similar problems where low level sound generally in the infrasonic range is generated, are detected and stored in a memory 61 disc (magnetic or optical), tape or in a chip (ROM). RAM 62 may be used to store current acoustic signals and signatures of the patient being examined.

When a condition of a binocular-visioned person having two eyes, one of which is injured or diseased, is diagnosed, infrasonic signals of both eyes are considered and the diagnosis includes comparing the infrasonic signals from the diseased or impaired eye with the infrasonic signals from the other eye of the binocular-visioned person. The front end of computer 56 includes a digital-to-analog converter 63, a preamplifier 64.

In a preferred embodiment of the invention, the signal is bandpass filtered and this can be done prior to the digital-to-analog conversion or in the computer 56. It will be appreciated that the infrasonic signals can also be processed on a purely analog basis as in FIG. 3. Since most of the signals of interest are in the infrasonic range (e.g., under about 15 Hz), they are preferably multiplied to a higher frequency range for easier processing and this can be done electronically in computer 56 or mechanically (e.g., a magnetically taped infrasonic recording is run at a higher speed (e.g. 5×-10×) during playback) to produce audible versions of the acoustic signature.

The heart beat of the subject can be detected by transducer 65, and an electrical signal corresponding to heart beat can be supplied to computer 56 for correlation with the infrasonic signals from transducers $T_R$ and $T_L$ and thus provide further diagnostic information for eye problems. In case of FIGS. 1-4, the heart beat signal can also be used to enhance the diagnostic process.

Figure 9:
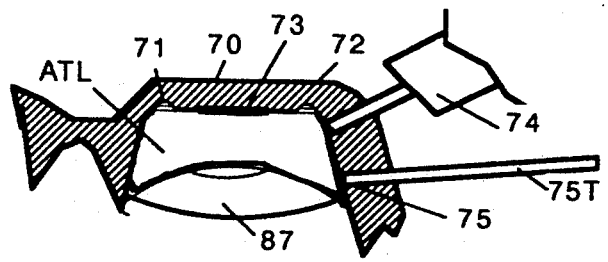

In FIGS. 5-7, the ATL reservoir is used when the subject or patient is in a prone or lying position. However, in order to take readings of the eye when the patient is standing or lying down, the embodiment of FIG. 9 is provided. In FIG. 9, a cover panel 70 is integrally formed or molded with the goggle eye pieces or reservoirs 52, 53 and is, in a preferred embodiment, provided with an annular groove 71 surrounding a transducer pedestal 72 carrying transducer 73. A syringe-like tool 74 is used to inject ATL into reservoir and/or air vent 75 on the forehead eyebrow end of the goggles when the liquid reaches the vent and starts to flow out, all air bubbles which could muffle or attenuate coupling of acoustic signals to the transducer are eliminated. The vent may be provided with a small transparent tube 75T as an indicator that the reservoir is full. Panel 70 closes off the vessels or reservoirs 52, 53 from ambient sounds.

Figure 10:
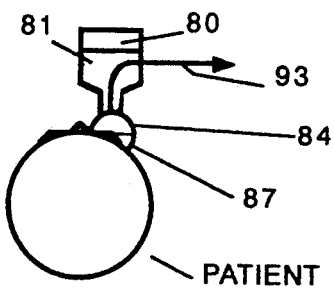
Figure 11:
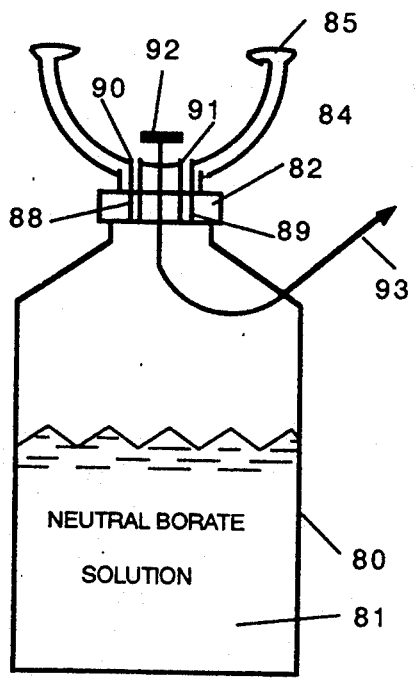
Figure 12:
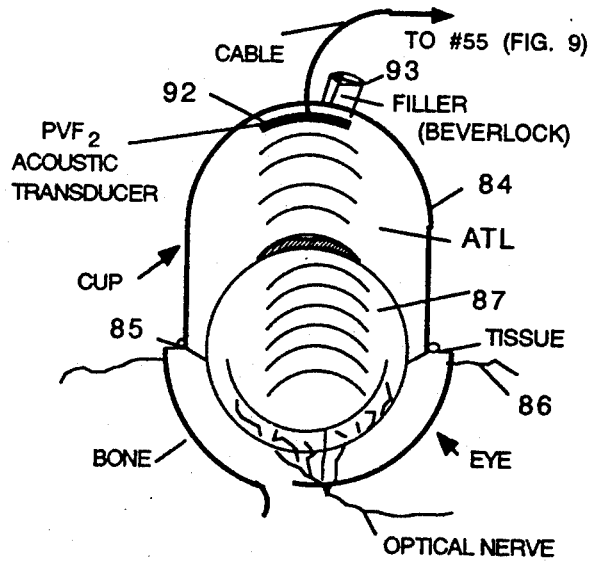

In another embodiment of the invention shown in FIGS. 10, 11 and 12, a commercial eye cup/container 80 containing a commercial eye wash solution 81, which in this embodiment is a neutral borate solution, as the ATL, has a cover 82 carrying eye cup 84 with an annular ring 85 for sealing engagement with the tissue structures 86 surrounding the eye 87. According to the invention, cover 82 is provided with a plurality of holes or openings 88, 89 which communicate with holes or openings 90, 91 in eye cup 84 to allow ATL liquid to flow freely into the eye cup when the container 80 is inverted. An acoustic transducer 92 is acoustically coupled by the ATL to the blood vessels in the eye. An interconnecting cable 93 carries the electrical signals produced by the transducer to the processing unit for display such as display 11 (FIG. 3) or 56D (FIG. 8). In FIG. 12, the eye cup is filled through a filler lock 93 by means of a syringe-like device 74 shown in FIG. 9.

In the preferred embodiment, the quantity of fluid in the reservoir is insufficient to place any significant pressure on the eye. In the preferred embodiment, the ATL is over the entire exposed surface so that a good acoustic couple is achieved. Moreover, even when the eyelid is closed, a good acoustic couple is achieved However, in this case, the retinal acoustic signals are stronger than those of the eyelid and care must be taken to discriminate between the two. It is preferred that for retinal blood flow, studies and diagnosis, the eyelid should be open to avoid detecting acoustic signals due to blood flow in the eyelid structures.

While there has been shown and described a preferred embodiment of the invention, it will be appreciated that various other adaptations and modifications of the invention will be readily apparent to those skilled in the art and it is intended to encompass such obvious modifications and adaptations in the spirit and scope of the claims appended hereto.

What is claimed is:

1. A non-invasive method of detecting ophthalmic conditions of a human eye comprising:
   1) immersing the exposed portion of the eyeball of said human body in an acoustically transmissive liquid (ATL),
   2) immersing a sonic transducer in the body of ATL and detecting infrasonic energy emitted by said eyeball constituting an acoustic signature of retinal blood flow to the eye, and
   3) storing said acoustic signature in a storage medium.

2. The invention defined in claim 1 wherein a predetermined number of said human eyes having known conditions are sequentially immersed in said ATL and acoustic signatures derived therefrom, respectively, and storing said acoustic signatures to form a library of acoustic signatures of retinal blood flow to the eye.

3. The invention defined in claim 2 including immersing a further human eye in an ATL and a further acoustic signature derived therefrom and comparing said further acoustic signature with said library of acoustic signatures to detect one or more particular conditions of said further human eye.

4. A non-invasive opthalmic apparatus comprising:
   a vessel for holding an acoustically transmissive liquid (ATL) in contact with the exposed portion of an eye of a patient, said vessel being of sufficient size to encompass said exposed portion of an eye in said acoustically transmissive liquid,
   said vessel having wall surfaces for sealingly engaging facial structures surrounding a human eye,
   transducer means in said vessel such that when said body of acoustically transmissive liquid is present in said vessel, said transducer means converts infrasonic acoustic energy travelling in said acoustically transmissive body of liquid to electrical signals,
   bandpass filter means connected to receive said electrical signals and to selectively filter the acoustic signature of retinal blood flow,
   means connected to said bandpass filter means for detecting said acoustic signatures of retinal blood flow in said human eye.

5. The invention defined in claim 4 wherein said transducer is a piezoelectric plastic having a flat frequency response in the infrasonic range.

6. The invention defined in claim 4 including means for storing a standard acoustic signature for retinal blood flow derived from a plurality of human eyes, and comparing subsequent acoustic signatures of retinal blood flow with said standard acoustic signature for retinal blood flow.

7. The invention defined in claim 4 including means for retaining said ATL in contact with said exposed portion of the eye and said transducer when the head of said patient is erect.

8. The invention defined in claim 4 wherein said transducer is mounted on a panel opposite said exposed portion and closing-off said vessel from ambient sounds.

9. The invention defined in claim 8 including syringe means for filling said vessel with ATL, and vent means on an upper surface of said vessel for indicating when all air bubbles between said transducer and said exposed eye portion have been removed.

10. The invention defined in claim 4 including means for detecting the heart beat of said patient.

11. A non-invasive method of diagnosing the condition of an eye, comprising:
   A. surrounding an eye cavity with an acoustically transmissive liquid medium,
   B. detecting infrasonic signals constituting an acoustic signature of retinal blood flow emitted by the eyeball in said acoustically transmissive medium,
   C. converting said infrasonic signals to an electrical signal, and
   D. analyzing said electrical signal to detect any eye diseases and/or injury.

12. The method defined in claim 11 wherein said eye is on a binocular visioned person having two eyes, one of which is injured or diseased, and including performing steps A, B and C on both eyes of said binocular visioned person, and
   E. said step D of analyzing includes comparing the electrical signals from said diseased or impaired eye with the other eye of said binocular visioned person.

13. The method defined in claim 11 wherein said step D of analyzing includes detecting one or more of the following, loss of blood flow to the retina, detachment of the retina, retinal bleeding, small hemorrhaging, and incipient eye problems.

14. The method defined in claim 11 including, between steps C and D, the step of multiplying said infrasonic signals to produce a higher frequency range for easier processing.

15. The method defined in claim 11 including detecting the heartbeat of a patient whose eye is being diagnosed.

* * * * *